US012678135B2

(12) United States Patent
Cornell

(10) Patent No.: US 12,678,135 B2
(45) Date of Patent: Jul. 14, 2026

(54) MULTI-COMPONENT HOUSING FOR SENSING IN INTRALUMINAL DEVICE

(71) Applicant: KONINKLIJKE PHILIPS N.V., Eindhoven (NL)

(72) Inventor: Blake Cornell, San Diego, CA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 18/853,576

(22) PCT Filed: Apr. 2, 2023

(86) PCT No.: PCT/EP2023/058601
§ 371 (c)(1),
(2) Date: Oct. 2, 2024

(87) PCT Pub. No.: WO2023/194269
PCT Pub. Date: Oct. 12, 2023

(65) Prior Publication Data
US 2025/0213219 A1 Jul. 3, 2025

Related U.S. Application Data

(60) Provisional application No. 63/328,355, filed on Apr. 7, 2022.

(51) Int. Cl.
*A61B 8/12* (2006.01)
*A61B 8/00* (2006.01)
*A61B 8/06* (2006.01)

(52) U.S. Cl.
CPC ............... *A61B 8/445* (2013.01); *A61B 8/06* (2013.01); *A61B 8/12* (2013.01)

(58) Field of Classification Search
CPC ......... A61B 8/12; A61B 8/445; A61B 8/4411; A61B 2562/182
See application file for complete search history.

(56) References Cited

U.S. PATENT DOCUMENTS

2010/0249602 A1* 9/2010 Buckley .................... A61B 8/12
600/467
2013/0231562 A1* 9/2013 Budzelaar .......... A61B 18/1492
600/439
(Continued)

FOREIGN PATENT DOCUMENTS

AU 2015201061 A1 3/2015
EP 3692893 A1 8/2020
(Continued)

OTHER PUBLICATIONS

International Search Report and Written Opinion of PCT/EP2023/058601, dated Jul. 20, 2023.

*Primary Examiner* — Colin T. Sakamoto

(57) ABSTRACT

An intraluminal device is provided, which includes a flexible elongate member configured to extend in a longitudinal direction within a body lumen of a patient, with a sensor disposed at a distal region of the flexible elongate member and facing in the longitudinal direction. The sensor is configured obtain intraluminal data associated with the body lumen. The intraluminal device includes a housing at least partially surrounding the sensor. The housing includes a distal portion including a first conductive material and a first dielectric material. The distal portion is fixedly attached to a different proximal portion which includes a second conductive material and a second dielectric material. The first conductive material and the second conductive material are in electrical communication with the sensor.

20 Claims, 11 Drawing Sheets

(56)     References Cited

U.S. PATENT DOCUMENTS

| 2016/0249817 A1* | 9/2016 | Mazar | A61B 5/6851 |
| | | | 600/486 |
| 2022/0133235 A1* | 5/2022 | Weekamp | A61B 5/026 |
| | | | 600/465 |

FOREIGN PATENT DOCUMENTS

| JP | H06178393 A | 6/1994 | |
| WO | WO-9937211 A1 * | 7/1999 | A61B 8/4461 |
| WO | WO-2020196427 A1 * | 10/2020 | A61B 8/12 |

* cited by examiner

MULTI-COMPONENT HOUSING FOR SENSING IN INTRALUMINAL DEVICE

TECHNICAL FIELD

The subject matter described herein relates to an improved sensor housing for physiology sensing intraluminal devices. This intraluminal measurement system has particular but not exclusive utility for intravascular catheters and guidewires.

BACKGROUND

Coronary artery disease (CAD) is among the world's leading causes of death. To address this problem, image guided therapy (IGT) makes use of a wide variety of imaging modalities (e.g., coronary angiography) as well as in-body diagnostic devices (e.g. pressure-sensing guidewires or intravascular ultrasound catheters). Small-diameter medical devices such as intraluminal (e.g., intravascular) catheters and guidewires may incorporate sensors (e.g., pressure, temperature, flow, or imaging sensors) whose power and communications occur through electrical conductor bundles. However, recent guidewire devices may in some cases have diameters of 360 microns or smaller. Current construction of such devices may require micro-cables/filars to be hand soldered/bonded to the sensor. Additionally, the subassembly consisting of the sensor and filars may be quite delicate. Even under high magnification, manual assembly of these assemblies may be extremely challenging, resulting in high scrap rates.

The information included in this Background section of the specification, including any references cited herein and any description or discussion thereof, is included for technical reference purposes only and is not to be regarded as subject matter by which the scope of the disclosure is to be bound.

SUMMARY

A blood flow velocity sensing guidewire can be used for example to assess Non-Obstructive Coronary Artery Disease (NOCAD) and Micro Vascular Disease (MVD). The present disclosure provides an improved sensor housing, constructed from both insulating and conductive materials, that facilitates a simpler assembly process with fewer manual steps. The sensor housing described herein has particular, but not exclusive, utility for intraluminal medical catheters and guidewires (e.g., intravascular catheter and catheters).

One general aspect includes an intraluminal device, which includes a flexible elongate member configured to extend in a longitudinal direction within a body lumen of a patient; a sensor disposed at a distal region of the flexible elongate member and facing in the longitudinal direction, where the sensor is configured obtain intraluminal data associated with the body lumen; and a housing at least partially surrounding the sensor, where the housing includes a distal portion fixedly attached to a different proximal portion. The distal portion includes a first conductive material and a first dielectric material, whereas the proximal portion includes a second conductive material and a second dielectric material, all configured such that the first conductive material and the second conductive material are in electrical communication with the sensor.

Implementations may include one or more of the following features. In some embodiments, the sensor includes an ultrasound transducer configured to emit ultrasound waves in the longitudinal direction while positioned within the body lumen and to receive echoes associated with the emitted ultrasound waves. In some embodiments, the distal portion of the housing further includes an acoustic matching layer formed of the first dielectric material. In some embodiments, the proximal portion of the housing further includes an acoustic backing layer formed of the second dielectric material. In some embodiments, the sensor includes a first electrode and a second electrode; the proximal portion of the housing includes a first electrical contact and a second electrical contact formed of the second conductive material; and the proximal portion of the housing or distal portion of the housing include: a first embedded conduction path formed of the first conductive material or the second conductive material and in electrical communication with the first electrical contact and the first electrode; and a second embedded conduction path formed of the first conductive material or the second conductive material and in electrical communication with the second electrical contact and the second electrode. In some embodiments, the first embedded conduction path and second embedded conduction path are at least partially surrounded by the first dielectric material or the second dielectric material. In some embodiments, the first electrical contact is attached to and in electrical communication with a first conductive filar positioned along the flexible elongate member; the second electrical contact is attached to and in electrical communication with a second conductive filar positioned along the flexible elongate member. In some embodiments, the distal portion of the housing includes an arresting feature that interacts with an arresting feature of the proximal portion of the housing to arrest rotation of the distal portion with respect to the proximal portion. In some embodiments, the sensor includes a central lumen aligned with the longitudinal direction, where the distal portion of the housing or proximal portion of the housing includes a central post passing through at least a portion of the central lumen, such that the sensor element is arrested from lateral motion with respect to the distal portion and proximal portion. In some embodiments, the flexible elongate member includes a core wire, and the proximal portion includes a core wire lumen configured to receive a distal portion of the core wire. In some embodiments, the distal portion of the core wire is fixedly attached within the core wire lumen. In some embodiments, the proximal portion of the housing is fixedly attached to the distal portion of the housing by an adhesive. In some embodiments, at least some interior volume of the proximal portion of the housing or distal portion of the housing is filled by the adhesive. In some embodiments, an outer surface of the sensor is fixedly attached to an inner surface of the proximal portion of the housing or distal portion of the housing by the adhesive. In some embodiments, a proximal edge of the distal portion of the housing forms a gap with a distal edge of the proximal portion of the housing. In some embodiments, the gap is at least partially filled by the adhesive. In some embodiments, the first conductive material and the second conductive material are a same material. In some embodiments, the first dielectric material is selected to have a desired acoustic impedance, and the second dielectric material is selected to have a desired acoustic absorptivity or reflectivity.

One general aspect includes an apparatus, which includes an intravascular guidewire including: a flexible elongate member configured to extend in a longitudinal direction within a blood vessel of a patient; and a flow sensor disposed at a distal region of the flexible elongate member, where the flow sensor includes: an ultrasound transducer configured to emit ultrasound waves in the longitudinal direction while positioned within the body lumen and to receive echoes associated with the ultrasound waves; a first electrode; and a second electrode. The apparatus also includes a housing at least partially surrounding the flow sensor. The housing includes a distal portion fixedly attached to a proximal portion, where the distal portion and proximal portion are different from one another. The distal portion of the housing includes: a first dielectric material; an acoustic matching layer including the first dielectric material; a distal conduction path including a first conductive material and in electrical communication with the first electrode of the flow sensor. The proximal portion of housing includes: a second dielectric material, an acoustic backing layer including the second dielectric material, a proximal conduction path including a second conductive material and in electrical communication with the second electrode of the sensor element, a first electrical contact positioned on a proximal surface of the proximal portion and in electrical communication with the proximal conduction path, and a second electrical contact positioned on the proximal surface of the proximal portion and in electrical communication with the distal conduction path.

This Summary is provided to introduce a selection of concepts in a simplified form that are further described below in the Detailed Description. This Summary is not intended to identify key features or essential features of the claimed subject matter, nor is it intended to limit the scope of the claimed subject matter. A more extensive presentation of features, details, utilities, and advantages of the flow measurement system, as defined in the claims, is provided in the following written description of various embodiments of the disclosure and illustrated in the accompanying drawings.

BRIEF DESCRIPTION OF THE DRAWINGS

Illustrative embodiments of the present disclosure will be described with reference to the accompanying drawings, of which.

DETAILED DESCRIPTION

Figure 1:
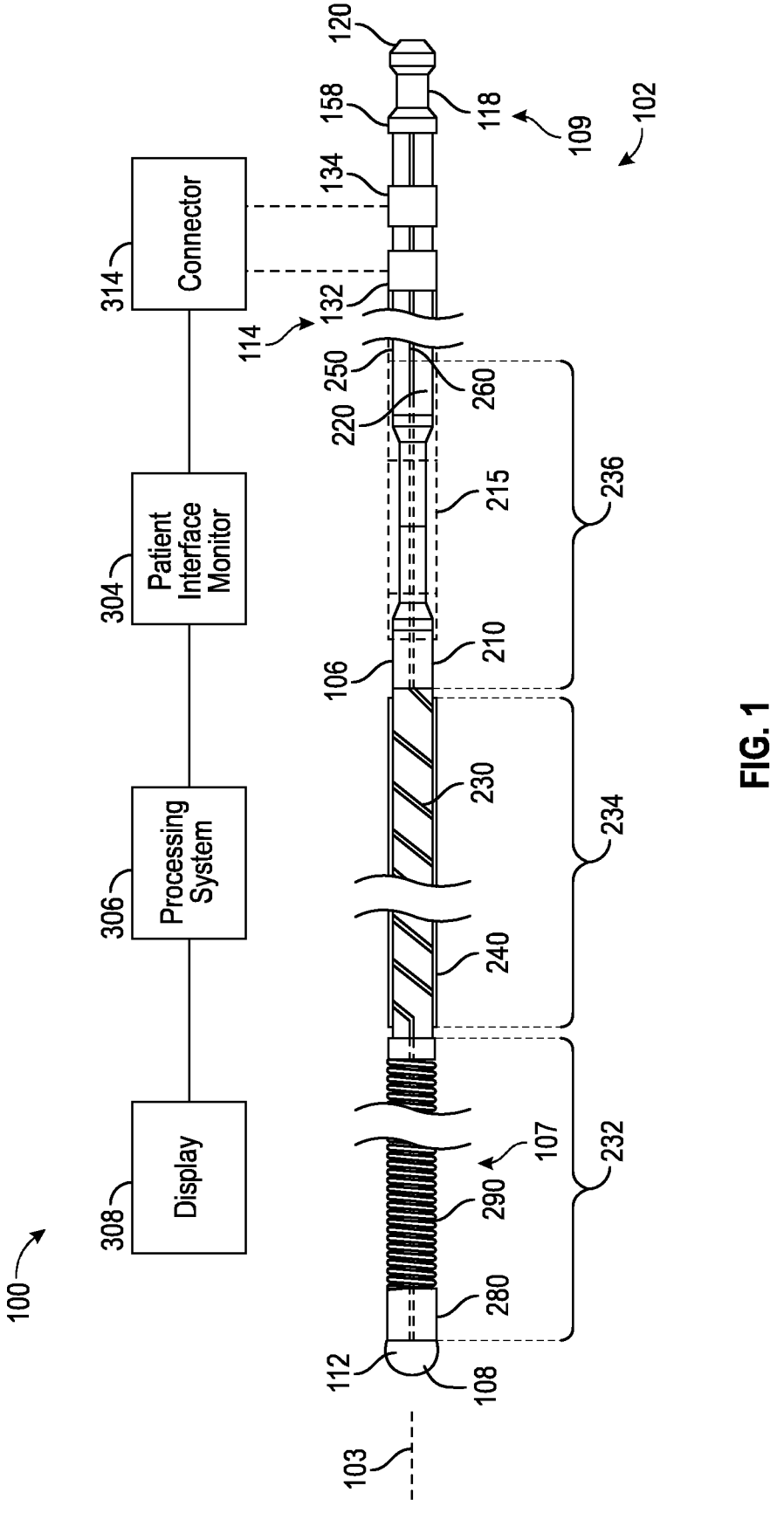
FIG. 1 is a diagrammatic side view of an intravascular sensing system that includes an intravascular device comprising an a multi-filar electrical conductor bundle, according to aspects of the present disclosure.

Coronary artery disease (CAD) is among the world's leading causes of death. To address this problem, Philips Image Guided Therapy (IGT) has a strong portfolio in imaging systems (for e.g. coronary angiography) as well as in-body diagnostic devices (e.g. pressure-sensing guidewires or intravascular ultrasound catheters). One such diagnostic device is the blood flow velocity sensing guidewire, which can be used for example to assess Non-Obstructive Coronary Artery Disease (NOCAD) and Micro Vascular Disease (MVD). These guidewires are equipped with a single-element ultrasound transducer that is located at its tip. The transducer can emit ultrasound waves in a forward-looking direction and receive the corresponding pulse-echo signals. By pulsed-wave (PW) Doppler analysis, the blood velocity distribution in a specific sampling volume can be deduced.

Existing sensor assemblies may include multiple components and multiple manual assembly steps that may require high dexterity and skill to perform, even under high magnification. The present disclosure provides an improved sensor housing or sensor assembly with fewer parts and thus a simpler assembly procedure that may be more amenable to automation. The design may also be significantly more robust than existing systems, with components being harder to damage during assembly, handling, or use. Producible through two-component or multi-component additive manufacturing (e.g., 3D printing), the sensor housing comprises a top portion and a bottom portion, each of which includes embedded conductors, insulators, acoustic layers (e.g., matching or backing layers), locking features, and sockets to receive a sensing element (e.g., an ultrasound transducer).

The present disclosure aids substantially in the fabrication and assembly of intraluminal sensing systems. Implemented on an ultrasound guidewire in communication with a processor, the sensor housing or sensor assembly disclosed herein provides a two-piece housing with imbedded wiring, that can be snapped together over the sensing element to produce a functional sensor. This improved design transforms a tedious, skill-intensive guidewire assembly process into a process that can be performed in less time, with less knowledge, less training, less manual dexterity, and fewer errors, without the normally routine need to manually solder components together. This unconventional approach improves the functioning of the flow-sensing guidewire, by reducing the chance of manufacturing errors.

These descriptions are provided for exemplary purposes only, and should not be considered to limit the scope of the flow measurement system. Certain features may be added, removed, or modified without departing from the spirit of the claimed subject matter.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. Additionally, while the description below may refer to blood vessels, it will be understood that the present disclosure is not limited to such applications. For example, the devices, systems, and methods described herein may be used in any body chamber or body lumen, including an esophagus, veins, arteries, intestines, ventricles, atria, or any other body lumen and/or chamber. For the sake of brevity, however, the numerous iterations of these combinations will not be described separately.

FIG. 1 is a diagrammatic side view of an intravascular sensing system 100 that includes an intravascular device 102 comprising a multi-filar electrical conductor bundle 230, according to aspects of the present disclosure. The intravascular device 102 can be an intravascular guidewire sized and shaped for positioning within a vessel of a patient. The intravascular device 102 can include a distal tip 108 and a sensing component 112. The sensing component 112 can be an electronic, electromechanical, mechanical, optical, and/or other suitable type of sensor. For example, the electronic component 112 can be a flow sensor configured to measure the velocity of blood flow within a blood vessel of a patient, a pressure sensor configured to measure a pressure of blood flowing within the vessel, or another type of sensor including but not limited to a temperature or imaging sensor. For example, flow data obtained by a flow sensor can be used to calculate physiological variables such as coronary flow reserve (CFR). Pressure data obtained by a pressure sensor may for example be used to calculate a physiological pressure ratio (e.g., FFR, iFR, Pd/Pa, or any other suitable pressure ratio). An imaging sensor may include an intravascular ultrasound (IVUS), intracardiac echocardiography (ICE), optical coherence tomography (OCT), or intravascular photoacoustic (IVPA) imaging sensor. For example, the imaging sensor can include one or more ultrasound transducer elements, including an array of ultrasound transducer elements.

The intravascular device 102 includes a flexible elongate member 106. The electronic component 112 is disposed at the distal portion 107 of the flexible elongate member 106. The electronic component 112 can be mounted at the distal portion 107 within a housing 280 in some embodiments. A flexible tip coil 290 extends distally from the housing 280 at the distal portion 107 of the flexible elongate member 106. A connection portion 114 located at a proximal end of the flexible elongate member 106 includes conductive portions 132, 134. In some embodiments, the conductive portions 132, 134 can be conductive ink that is printed and/or deposited around the connection portion 114 of the flexible elongate member 106. In some embodiments, the conductive portions 132, 134 are conductive, metallic rings that are positioned around the flexible elongate member. A locking section is formed by collar 118 and knob 120 are disposed at the proximal portion 109 of the flexible elongate member 106.

The intravascular device 102 in FIG. 1 includes a distal core wire 210 and a proximal core wire 220. The distal core 210 and the proximal core 220 are metallic components forming part of the body of the intravascular device 102. For example, the distal core 210 and the proximal core 220 are flexible metallic rods that provide structure for the flexible elongate member 106. The diameter of the distal core 210 and the proximal core 220 can vary along its length. A joint between the distal core 210 and proximal core 220 is surrounded and contained by a hypotube 215.

In some embodiments, the intravascular device 102 comprises a distal assembly and a proximal assembly that are electrically and mechanically joined together, which provides for electrical communication between the electronic component 112 and the conductive portions 132, 134. For example, flow data obtained by the electronic component 112 (in this example, electronic component 112 is a flow sensor) can be transmitted to the conductive portions 132, 134. Control signals (e.g., operating voltage, start/stop commands, etc.) from a processor system 306 in communication with the intravascular device 102 can be transmitted to the electronic component 112 via a connector 314 that is attached to the conductive portions 132, 134. The distal subassembly can include the distal core 210. The distal subassembly can also include the electronic component 112, the multi-filar conductor bundle 230, and/or one or more layers of insulative polymer/plastic 240 surrounding the conductive members 230 and the core 210. For example, the polymer/plastic layer(s) can insulate and protect the conductive members of the multi-filar cable or conductor bundle 230. The proximal subassembly can include the proximal core 220. The proximal subassembly can also include one or more layers of polymer layer(s) 250 (hereinafter polymer layer 250) surrounding the proximal core 220 and/or conductive ribbons 260 embedded within the one or more insulative and/or protective polymer layer(s) 250. In some embodiments, the proximal subassembly and the distal subassembly can be separately manufactured. During the assembly process for the intravascular device 102, the proximal subassembly and the distal subassembly can be electrically and mechanically joined together. As used herein, flexible elongate member can refer to one or more components along the entire length of the intravascular device 102, one or more components of the proximal subassembly (e.g., including the proximal core 220, etc.), and/or one or more components the distal subassembly 210 (e.g., including the distal core 210, etc.). The joint between proximal core 220 and distal core 210 is surrounded by the hypotube 215.

In various embodiments, the intravascular device 102 can include one, two, three, or more core wires extending along its length. For example, in one embodiment, a single core wire extends substantially along the entire length of the flexible elongate member 106. In such embodiments, a locking section 118 and a section 120 can be integrally formed at the proximal portion of the single core wire. The electronic component 112 can be secured at the distal portion of the single core wire. In other embodiments, such as the embodiment illustrated in FIG. 1, the locking section 118 and the section 120 can be integrally formed at the proximal portion of the proximal core 220. The electronic component 112 can be secured at the distal portion of the distal core 210. The intravascular device 102 includes one or more conductive members in a multi-filar conductor bundle 230 in communication with the electronic component 112. For example, the conductor bundle 230 can include one or more electrical wires that are directly in communication with the electronic component 112. In some instances, the conductive members 230 are electrically and mechanically coupled to the electronic component 112 by, e.g., soldering. In some instances, the conductor bundle 230 comprises two or three electrical wires (e.g., a bifilar cable or a trifilar cable). An individual electrical wire can include a bare metallic conductor, or a metallic conductor surrounded by one or more insulating layers. The multi-filar conductor bundle 230 can extend along a length of the distal core 210. For example, at least a portion of the conductive members 230 can be helically, or spirally, wrapped around an entire length of the distal core 210, or a portion of the length of the distal core 210.

The intravascular device 102 includes one or more conductive ribbons 260 at the proximal portion of the flexible elongate member 106. The conductive ribbons 260 are embedded within polymer layer(s) 250. The conductive ribbons 260 are directly in communication with the conductive portions 132 and/or 134. In some instances, the multi-filar conductor bundle 230 is electrically and mechanically coupled to the electronic component 112 by, e.g., soldering. In some instances, the conductive portions 132 and/or 134 comprise conductive ink (e.g., metallic nano-ink, such as silver or gold nano-ink) that is deposited or printed directed over the conductive ribbons 260.

As described herein, electrical communication between the conductive members 230 and the conductive ribbons 260 can be established at the connection portion 114 of the flexible elongate member 106. By establishing electrical communication between the conductor bundle 230 and the conductive ribbons 260, the conductive portions 132, 134 can be in electrically communication with the electronic component 112.

In some embodiments represented by FIG. 1, intravascular device 102 includes a locking section 118 and a section 120. To form locking section 118, a machining process is necessary to remove polymer layer 250 and conductive ribbons 260 in locking section 118 and to shape proximal core 220 in locking section 118 to the desired shape. As shown in FIG. 1, locking section 118 includes a reduced diameter while section 120 has a diameter substantially similar to that of proximal core 220 in the connection portion 114. In some instances, because the machining process removes conductive ribbons in locking section 118, proximal ends of the conductive ribbons 260 would be exposed to moisture and/or liquids, such as blood, saline solutions, disinfectants, and/or enzyme cleaner solutions, an insulation layer 158 is formed over the proximal end portion of the connection portion 114 to insulate the exposed conductive ribbons.

In some embodiments, a connector 314 provides electrical connectivity between the conductive portions 132, 134 and a patient interface module or patient interface monitor 304. The patient interface monitor (PIM) 304 may in some cases connect to a console or processing system 306, which includes or is in communication with a display 308. In some embodiments, the patient interface monitor 304 includes signal processing circuitry, such as an analog-to-digital converter (ADC), analog and/or digital filters, signal conditioning circuitry, and any other suitable signal processing circuitry for processing the signals provided by the electronic component 112 for use by the processing system 306.

The system 100 may be deployed in a catheterization laboratory having a control room. The processing system 306 may be located in the control room. Optionally, the processing system 306 may be located elsewhere, such as in the catheterization laboratory itself. The catheterization laboratory may include a sterile field while its associated control room may or may not be sterile depending on the procedure to be performed and/or on the health care facility. In some embodiments, device 102 may be controlled from a remote location such as the control room, such than an operator is not required to be in close proximity to the patient.

The intraluminal device 102, PIM 304, and display 308 may be communicatively coupled directly or indirectly to the processing system 306. These elements may be communicatively coupled to the medical processing system 306 via a wired connection such as a standard copper multi-filar conductor bundle 230. The processing system 306 may be communicatively coupled to one or more data networks, e.g., a TCP/IP-based local area network (LAN). In other embodiments, different protocols may be utilized such as Synchronous Optical Networking (SONET). In some cases, the processing system 306 may be communicatively coupled to a wide area network (WAN).

The PIM 304 transfers the received signals to the processing system 306 where the information is processed and displayed on the display 308. The console or processing system 306 can include a processor and a memory. The processing system 306 may be operable to facilitate the features of the intravascular sensing system 100 described herein. For example, the processor can execute computer readable instructions stored on the non-transitory tangible computer readable medium.

The PIM 304 facilitates communication of signals between the processing system 306 and the intraluminal device 102. In some embodiments, the PIM 304 performs preliminary processing of data prior to relaying the data to the processing system 306. In examples of such embodiments, the PIM 304 performs amplification, filtering, and/or aggregating of the data. In an embodiment, the PIM 304 also supplies high- and low-voltage DC power to support operation of the intraluminal device 102 via the multi-filar conductor bundle 230.

The multi-filar cable or transmission line bundle 230 can include a plurality of conductors, including one, two, three, four, five, six, seven, or more conductors. The multi-filar conductor bundle 230 can be positioned along the exterior of the distal core 210. The multi-filar conductor bundle 230 and the distal core 210 can be overcoated with an insulative and/or protective polymer 240. In the example shown in FIG. 1, the multi-filar conductor bundle 230 includes two straight portions 232 and 236, where the multi-filar conductor bundle 230 extends linearly and parallel to a longitudinal axis 103 of the flexible elongate member 106 on the exterior of the distal core 210, and a helical or spiral portion 234, where the multi-filar conductor bundle 230 is wrapped around the exterior of the distal core 210. In some embodiments, the multi-filar conductor bundle 230 only includes a straight portion or only includes a helical or spiral portion. In general, the multi-filar conductor bundle 230 can extend in a linear, wrapped, non-linear, or non-wrapped manner, or any combination thererof. Communication, if any, along the multi-filar conductor bundle 230 may be through numerous methods or protocols, including serial, parallel, and otherwise, wherein one or more filars of the bundle 230 carry signals. One or more filars of the multi-filar conductor bundle 230 may also carry direct current (DC) power, alternating current (AC) power, or serve as an electrical ground connection.

The display or monitor 308 may be a display device such as a computer monitor, a touch-screen display, a television screen, or any other suitable type of display. The monitor 308 may be used to display selectable prompts, instructions, and visualizations of imaging data to a user. In some embodiments, the monitor 308 may be used to provide a procedure-specific workflow to a user to complete an intraluminal imaging procedure.

Before continuing, it should be noted that the examples described above are provided for purposes of illustration, and are not intended to be limiting. Other devices and/or device configurations may be utilized to carry out the operations described herein.

Figure 2:
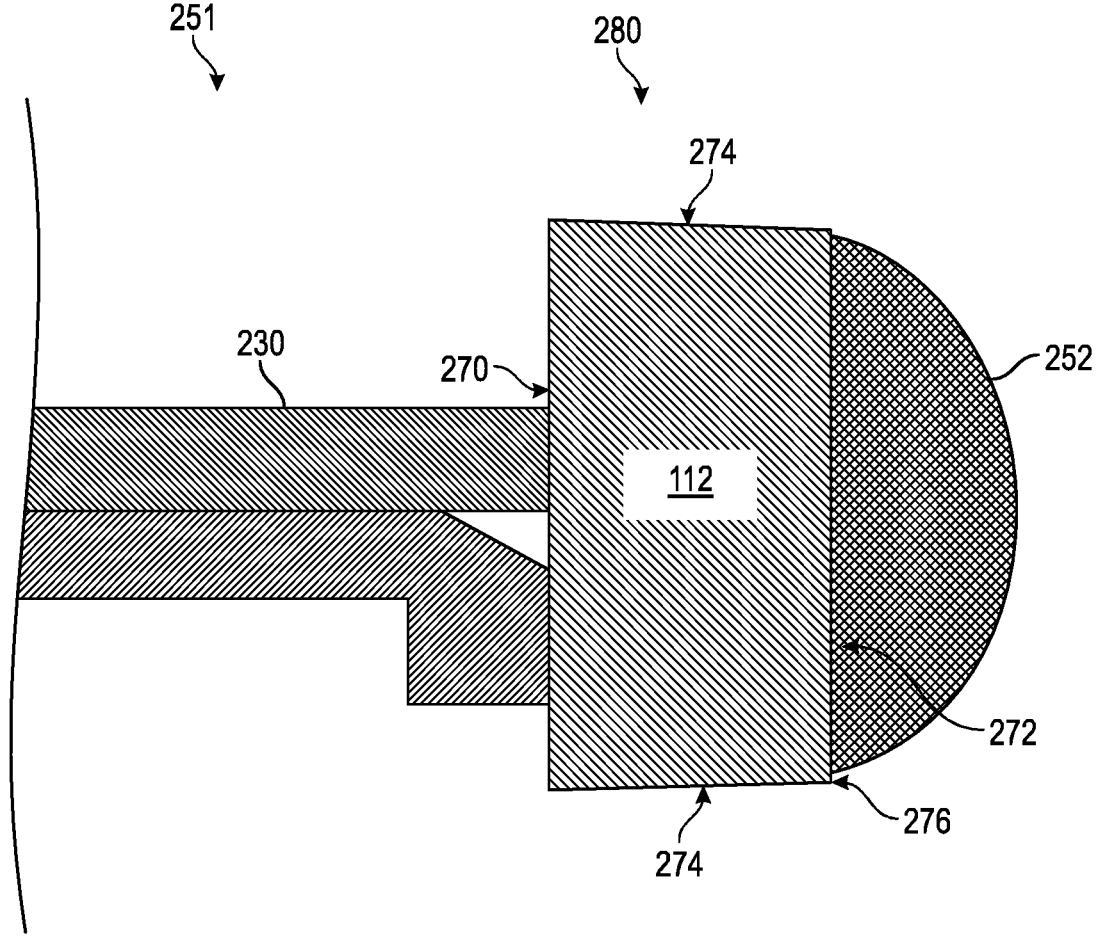
FIG. 2 is a perspective view of an example electronic component of an intravascular device, in accordance with aspects of the present disclosure.

FIG. 2 is a diagrammatic cross-sectional view of an example sensor assembly 251, which may for example be included in the intravascular device 102 of FIG. 1. More specifically, FIG. 2 illustrates a sensor assembly 251 that includes a sensing component 112, a housing 280, and an acoustic matching layer 252. As indicated by the positions of the sensing component 112 and the housing 280 illustrated in FIG. 1, the sensor assembly 251 may be included in a distal portion of the intravascular device 102 such that the surface 272 of the sensing component 112 faces distally.

As illustrated in FIG. 2, the sensing component 112 is positioned within the housing 280 and includes a proximal surface 270, an opposite, distal surface 272, and a side surface 274. In some embodiments, one or more of the proximal surface 270, the distal surface 272, or the side surface 274 may be coated in an insulating layer 276. The insulating layer 276 may be formed from parylene, which may be deposited on the one or more surfaces, for example. The insulating layer 276 may additionally or alternatively be formed from any other suitable insulating material. In some embodiments, the insulating layer 276 may prevent a short (e.g., an electrical failure), which may otherwise be caused by contact between a conductive portion of the sensing component 112 and the housing 280, which may be formed with a metal. As used herein, references to the distal surface 272 encompass the insulating layer 276 in embodiments where a distal end of the sensing component 112 is covered by the insulating layer 276, references to the proximal surface 270 encompass the insulating layer in embodiments where a proximal end of the sensing component 112 is covered by the insulating layer 276, and references to the side surface 274 encompass the insulating layer in embodiments where the side of the sensing component 112 is covered by the insulating layer 276 unless indicated otherwise.

In some embodiments, the sensing component 112 may include a transducer element, such as an ultrasound transducer element on the distal surface 272 such that the transducer element faces distally and may be used by the sensing component 112 to obtain sensor data corresponding to a structure distal of the sensing component 112. The sensing component 112 may additionally or alternatively include a transducer element on the proximal surface 270 such that the transducer faces proximally and may be used to obtain sensor data corresponding to a structure proximal of the sensing component. A transducer element may additionally or alternatively be positioned on a side surface 274 (e.g., on a perimeter or circumference) of the sensing component 112 in some embodiments. In some embodiments, a transducer and its associated electrodes and electrical connection points may form the entire sensing component 112, such that all surfaces of the sensing component 112 comprise the transducer.

As further illustrated, the sensing component 112 is coupled to the multi-filar conductor bundle 230, and at least a portion (e.g., a distal portion) of the multi-filar conductor bundle 230 are extends through the housing 280. In some embodiments, the multi-filar conductor bundle 230 and the sensing component 112 may be physically (e.g., mechanically) coupled. Further, one or more filars (e.g., conductive members) of the multi-filar conductor bundle 230 may electrically couple to (e.g., be in electrical communication) with the sensing component 112. In particular, one or more filars of the multi-filar conductor bundle 230 may couple to an element, such as a transducer (e.g., an ultrasound transducer), of the sensing component 112 and may provide power, control signals, an electrical ground or signal return, and/or the like to the element. As described above, such an element may be positioned on the distal surface 272 of the sensor. In that regard, in some embodiments, one or more filars of the multi-filar conductor bundle 230 may extend through a cutout or hole in the sensing component 112 (e.g., in at least the proximal surface 270) to establish electrical communication with an element on the distal surface 272 of the sensor. Filars may additionally or alternatively wrap around the side surface 274 to establish electrical communication with the element on the distal surface 272. Moreover, in some embodiments, filars of the multi-filar conductor bundle 230 may terminate at and/or electrically couple to the proximal surface 270 (e.g., to an element on the proximal surface 270) of the sensing component 112. Further, in some embodiments, a subset of the filars of the multi-filar conductor bundle 230 may extend to the distal surface 272 and/or electrically couple to an element at the distal surface 272, while a different subset of the filars may electrically couple to an element at the proximal surface 270, for example.

In some embodiments, the multi-filar conductor bundle 230 may be coated in the insulating layer 276. In some embodiments, for example, the multi-filar conductor bundle 230 and the sensing component 112 may be coupled together in a sub-assembly before being positioned in the housing 280. In such embodiments, the insulating layer 276 may be applied (e.g., coated and/or deposited) onto the entire sub-assembly, resulting in an insulating layer 276 on both the sensing component 112 and the multi-filar conductor bundle 230.

In some embodiments, the acoustic matching layer 252 may be positioned on (e.g., over) the distal surface 272 of the sensing component 112. In particular, the acoustic matching layer 252 may be disposed directly on the sensing component 112, or the acoustic matching layer 252 may be disposed on the insulating layer 276 coating the sensing component 112. Further, the acoustic matching layer 252 may be disposed on a transducer element (e.g., an ultrasound transducer element) positioned on the sensing component (e.g., the distal surface 272) and/or at least a portion of a conductive filar of the multi-filar conductor bundle 230 that is in communication with the transducer element, such as a filar extending through a hole or along a side of the sensing component 112. To that end, the acoustic matching layer 252 may contact and/or at least partially surround the portion of the conductive filar and/or the transducer element. Moreover, the acoustic matching layer 252 may provide acoustic matching to the sensing component 112 (e.g., to an ultrasound transducer of the sensing component 112). For instance, the acoustic matching layer 252 may minimize acoustic impedance mismatch between the ultrasound transducer and a sensed medium, such as a fluid and/or a lumen that the intravascular device 102 is positioned within. In that regard, the acoustic matching layer 252 may be formed from any suitable material, such as a polymer or an adhesive, to provide acoustic matching with the sensing component 112. The portion of the acoustic matching layer 252 positioned on the distal surface 272 may include and/or be formed from the same material as a portion of the acoustic matching layer positioned on the side surface 274 and/or the proximal surface 270. Further, the acoustic matching layer 252 may be applied to the sensing component 112 before or after the sensing component 112 is positioned within the housing 280 during assembly of the sensor assembly 251. In this regard, the portion of the acoustic matching layer 252 positioned on the distal surface 272 and the portion of the acoustic matching layer positioned on the side surface 274 and/or the proximal surface 270 may be included in the sensor assembly 251 in the same or different steps. Further, in addition to the one or more materials the acoustic matching layer 252 is formed from, the acoustic matching layer 252 may provide acoustic matching with the sensing component 112 via one or more dimensions of the acoustic matching layer 252.

In some embodiments, the sensor assembly 251 may include an atraumatic tip, such as the distal tip 108 illustrated in FIG. 1. In some embodiments, the distal tip 108 may include the same material as the acoustic matching layer 252. In some embodiments, the distal tip may include a different material than the acoustic matching layer 252. Additionally or alternatively the distal tip 108 may be formed from one or more layers of materials. The layers may include different materials and/or different configurations (e.g., shape and/or profile, thickness, and/or the like). Further, the distal tip 108 may be arranged to cover the distal surface 272 of the sensing component 112. In some embodiments, the distal tip 108 may also cover a distal end 272 of the housing 280. Moreover, while the distal tip 108 is illustrated as having a domed shape, embodiments are not limited thereto. In this regard, the distal tip 108 may include a flattened profile or any suitable shape. In some embodiments, the entire sensing component 112 may be positioned within (e.g., surrounded by the continuous surface of) the housing 280.

Figure 3A:
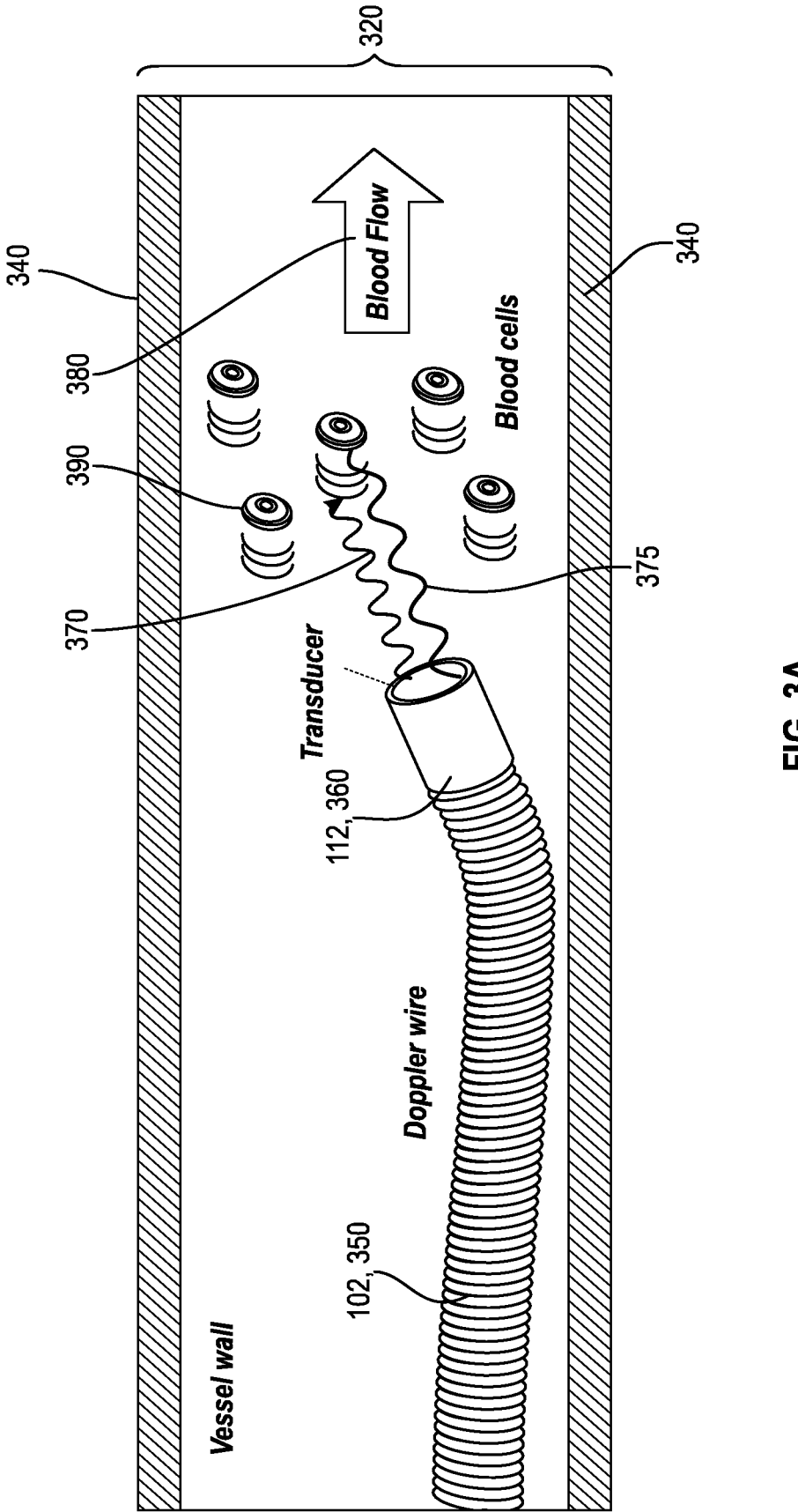
FIG. 3A is a schematic view of an intravascular during measurement of a flow velocity inside a blood vessel, in accordance with at least one embodiment of the present disclosure.

FIG. 3A is a schematic view of an intravascular device 102 (e.g., a flow-sensing guidewire 350) during measurement of a flow velocity 380 inside a blood vessel 320 with blood vessel walls 340, in accordance with at least one embodiment of the present disclosure. In the example shown in FIG. 3A, the sensor 112 (e.g., an ultrasound transducer 360) at the tip is shown to emit ultrasound waves 370 that are backscattered as reflections 375 by flowing cells 390 in the blood and sensed by the transducer 360.

Figure 3B:
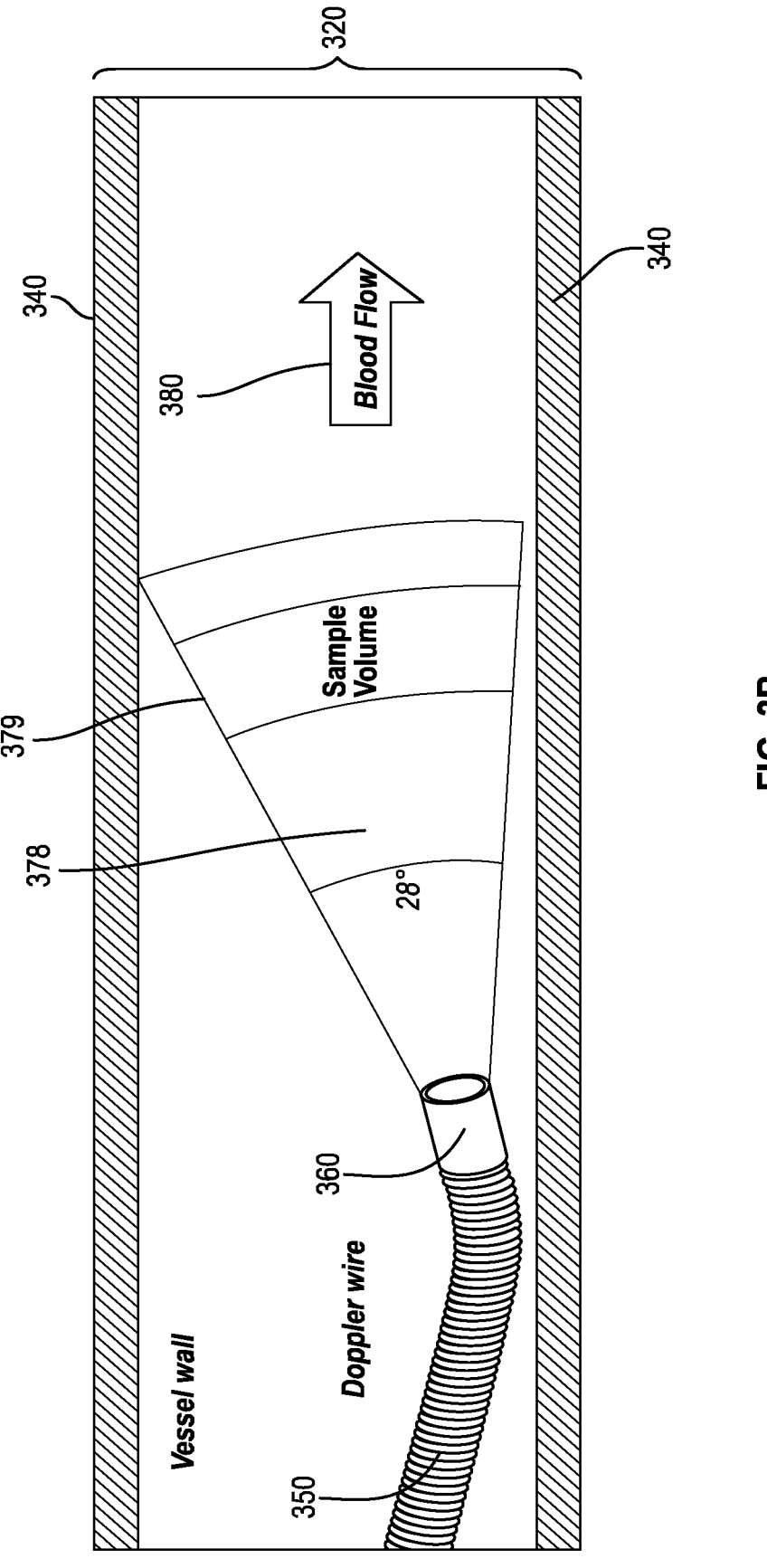
FIG. 3B is a schematic view of an intravascular device during measurement of a flow velocity inside a blood vessel, in accordance with at least one embodiment of the present disclosure.

FIG. 3B is a schematic view of an intravascular device 102 (e.g., a flow-sensing guidewire 350) during measurement of a flow velocity 380 inside a blood vessel 320 with blood vessel walls 340, in accordance with at least one embodiment of the present disclosure. In the example shown in FIG. 3B, the beam profile or viewing cone 378 of the transducer 360 is schematically shown, along with an example of the sample volume 379 over which the distribution of the flow velocity 380 is measured. This sample volume 379 results from the transducer beam profile or viewing cone 378 as well as the selected measurement distance range, as described below.

Figure 4:
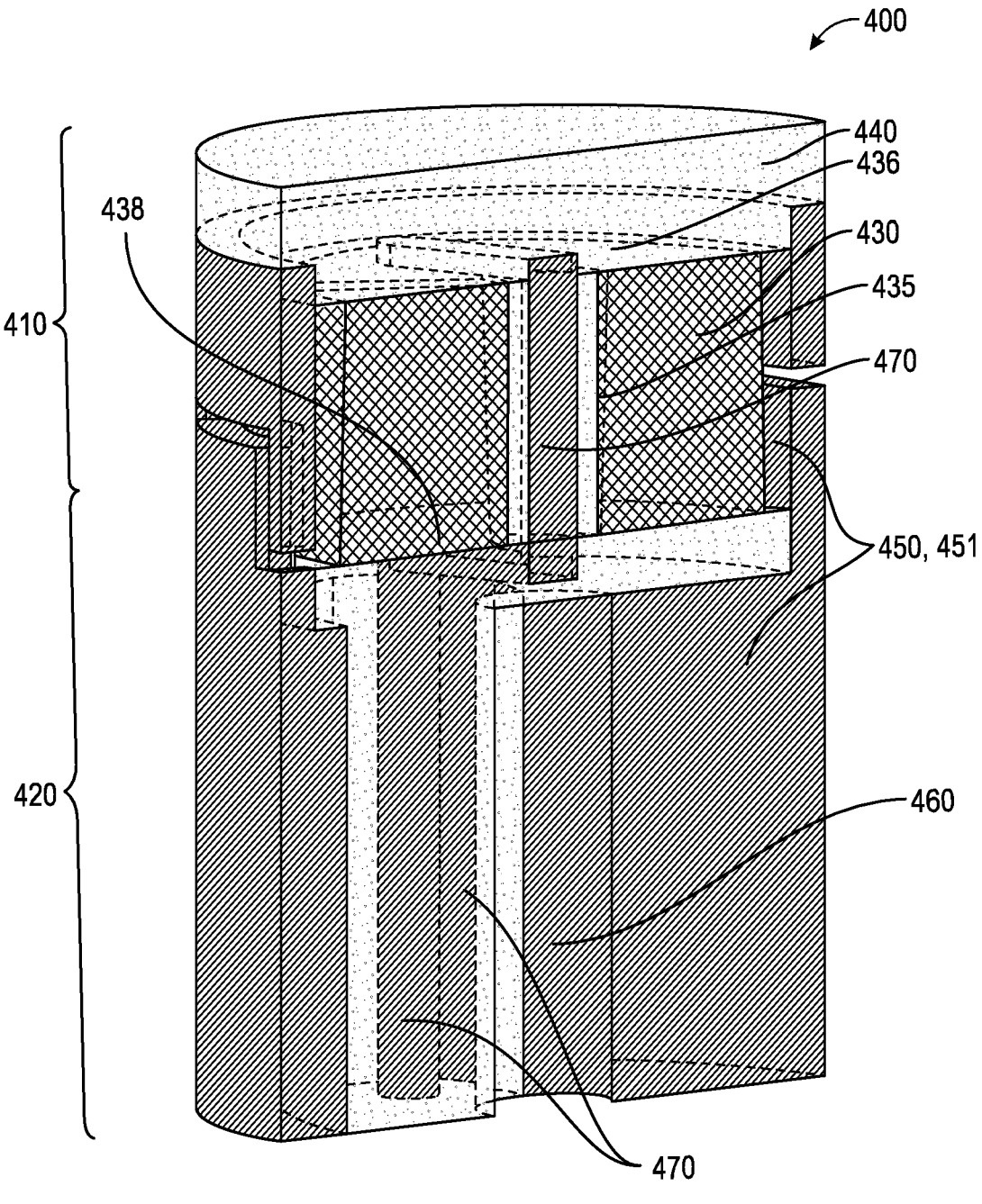
FIG. 4 is a diagrammatic cross-sectional view of an example sensor housing or sensor assembly, in accordance with at least one embodiment of the present disclosure.

FIG. 4 is a diagrammatic cross-sectional view of an example sensor housing or sensor assembly 400, in accordance with at least one embodiment of the present disclosure. The sensor housing or sensor assembly 400 may in some cases be similar to sensor assembly 251 or sensor housing 280 of FIG. 1. The sensor housing or sensor assembly 400 comprises a top portion or distal portion 410 and a bottom portion or proximal portion 420, which together enclose a sensor element 430, such as an ultrasound transducer, which may in some cases be similar to sensing element 112 of FIG. 2. In some embodiments, the sensor element 430 includes a central lumen 435, a top electrode 436, and a bottom electrode 438. The top electrode 436 may for example include a conductive material coated over all or part of the top surface of the sensor element 430. The bottom electrode 438 may for example include a conductive material coated over all or part of the bottom surface of the sensor element 430. The sensor element 430 may for example include a piezoelectric material, a capacitive micromachined ultrasound transducer (CMUT), a photoacoustic sensor, or other sensor.

The top portion 410 includes an acoustic matching layer 440, which may in some cases be similar to acoustic matching layer 252 of FIG. 2. The bottom portion 420 includes a core wire lumen 460, into which a core wire (e.g., distal core wire 210 of FIG. 1) can be inserted. In some embodiments, the bottom portion 420 is attached to the core wire with an adhesive or potting compound. Both the top portion 410 and the bottom portion 420 include embedded conductors 470, which will be described in more detail below. The top portion 410 and bottom portion 420 also include an interior portion 450, which may comprise a metallic material as shown, or may for example be at least partially filled with an adhesive, potting compound 451 or other insulating material.

In an example, the top portion 410 and bottom portion 420 are produced separately, and then snapped and/or adhered together around the sensor element 430. In an example, the top portion and bottom portion are each produced as a stack of horizontal layers, via microscale two-component or multi-component additive manufacturing, where at least one component is conductive (e.g., metallic) and at least one other component is insulating or dielectric (e.g., polymer, ceramic, composite, etc.). Individual layers may for example be 1-50 microns in thickness, with horizontal feature sizes or voxel sizes of 10-30 microns, although other thicknesses and feature sizes, both larger and smaller, may be used instead or in addition.

Figure 5B:
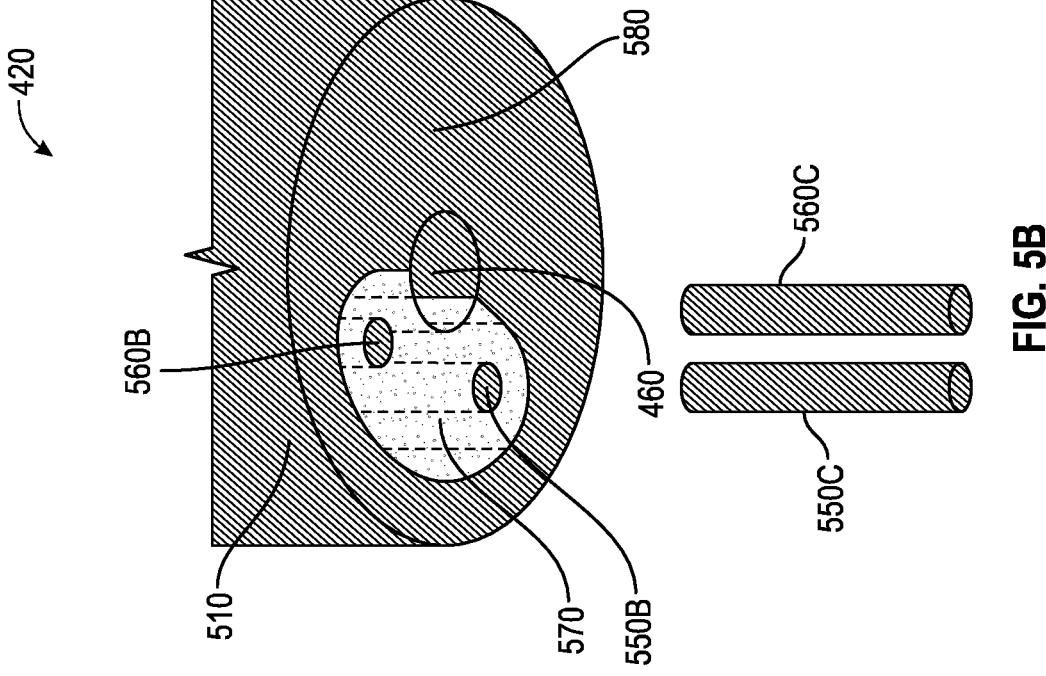
FIG. 5B is a diagrammatic bottom perspective view of at least a portion of an example bottom portion of a sensor housing or sensor assembly, in accordance with at least one embodiment of the present disclosure.
Figure 5A:
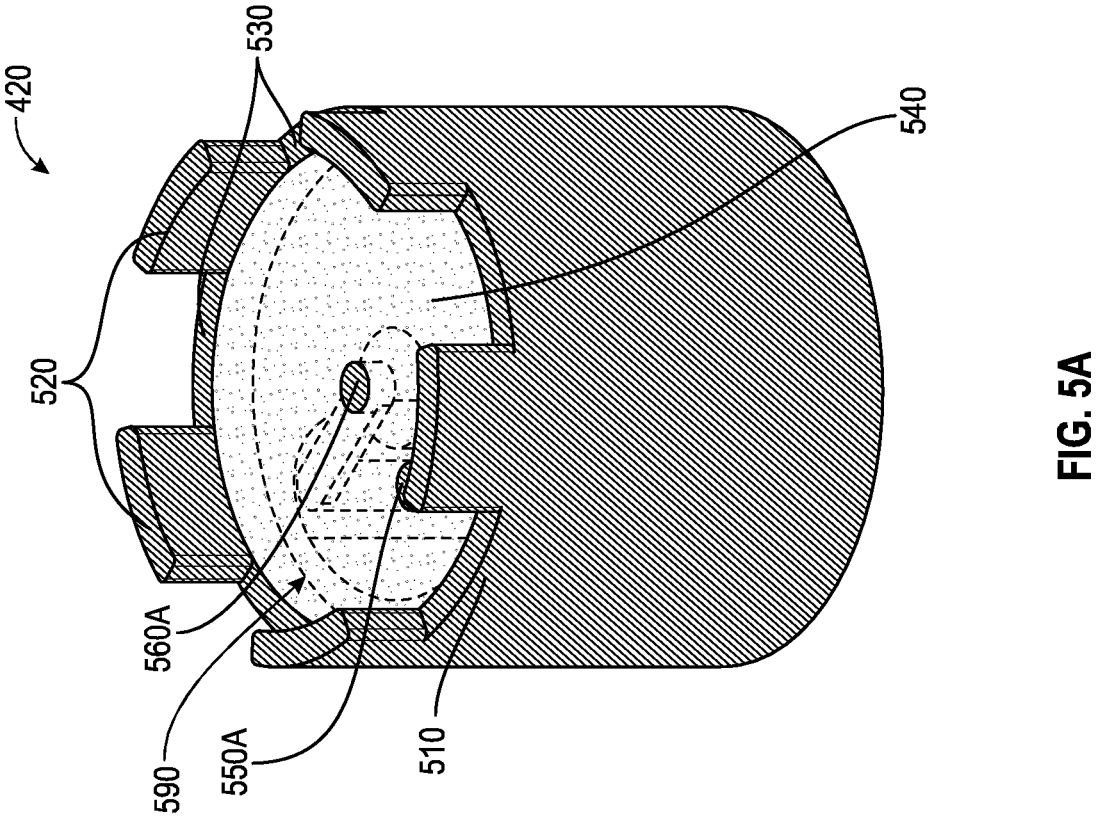
FIG. 5A is a diagrammatic top perspective view of an example bottom portion of a sensor housing or sensor assembly, in accordance with at least one embodiment of the present disclosure.

FIG. 5A is a diagrammatic top perspective view of an example bottom portion 420 of a sensor housing or sensor assembly 400, in accordance with at least one embodiment of the present disclosure. In an example, the bottom portion 420 is generally cylindrical in shape, to facilitate movement through blood vessels or other body lumens, although other shapes (e.g., polygonal prisms or other appropriate shapes) may be used instead or in addition. The bottom portion 420 includes a sidewall 510, which may in some cases be similar to side surface 274 of FIG. 2. In the example shown in FIG. 5A, the sidewall 510 is topped by crenelations 520, which are interspersed with recesses 530. Any number of crenelations 520 and recesses 530 may be used, from one to several dozen, although ranges between 3 and 8 may be preferred. In an example, the crenelations 520 and recesses 530 interlock with similar features on the top portion 410, to arrest rotation of the top portion 410 and bottom portion 420 with respect to one another. It should be understood that these particular features are shown here for exemplary purposes. Other arresting or interlocking features may be used instead or in addition, including but not limited to pegs and indentations, saw teeth, threads, pins and grooves, etc.

In the example shown in FIG. 5A, the bottom portion also includes an acoustic backing layer 540, along with a bottom electrode contact 550A and a top electrode contact 560A. The crenelations 520, acoustic backing layer 540, bottom electrode contact 550A and top electrode contact 560A collectively form a bottom socket 590, configured to receive the sensor element 430 (see FIG. 4). In an example, the sidewall 510, crenelations 520, recesses 530, and contacts 550A and 550B are made of a conductive material such as a metal, a doped semiconductor, a doped ceramic, or a doped polymer. In other examples, the sidewall 510, crenelations 520, and recesses 530 are made of an insulating material. In some embodiments, the outer surface of the sidewall 510 is a patient-contacting surface that may, for example, come into contact with the walls of a blood vessel. For this reason, it may be desirable for the sidewall 510 to present a smooth, atraumatic outer surface that moves easily through blood vessels without causing damage.

FIG. 5B is a diagrammatic bottom perspective view of at least a portion of an example bottom portion 420 of a sensor housing or sensor assembly 400, in accordance with at least one embodiment of the present disclosure. The bottom portion 420 includes a sidewall 510 and a bottom surface 580, which may in some cases be similar to proximal surface 270 of FIG. 2. The bottom surface 580 includes a bottom electrode contact 550B and a top electrode contact 560B, both of which are embedded in an insulating column 570. In some embodiments, the bottom electrode contact 550B and top electrode contact 560B are respectively in electrical communication with bottom contact electrode 550A and top electrode contact 560A (see FIG. 5A) via embedded conductors (see FIG. 6A).

In an example, filars 550C and 560C of the multi-filar conductor bundle 230 (see FIG. 2) can be attached to the bottom electrode contact 550B and top electrode contact 560B, respectively, such that they are in electrical contact, and such that the bottom electrode contact 550B and top electrode contact 560B are in electrical communication with the Patient Interface Monitor 304 via the multi-filar conductor bundle 230, conductive ribbons 260, conductive portions 132 and 134, and connector 314 (see FIG. 1). Attachment of the filars 550C and 560C to the electrode contacts 550B and 560B can be by soldering, welding, ultrasonic welding, conductive adhesive, or other means.

Figure 6A:
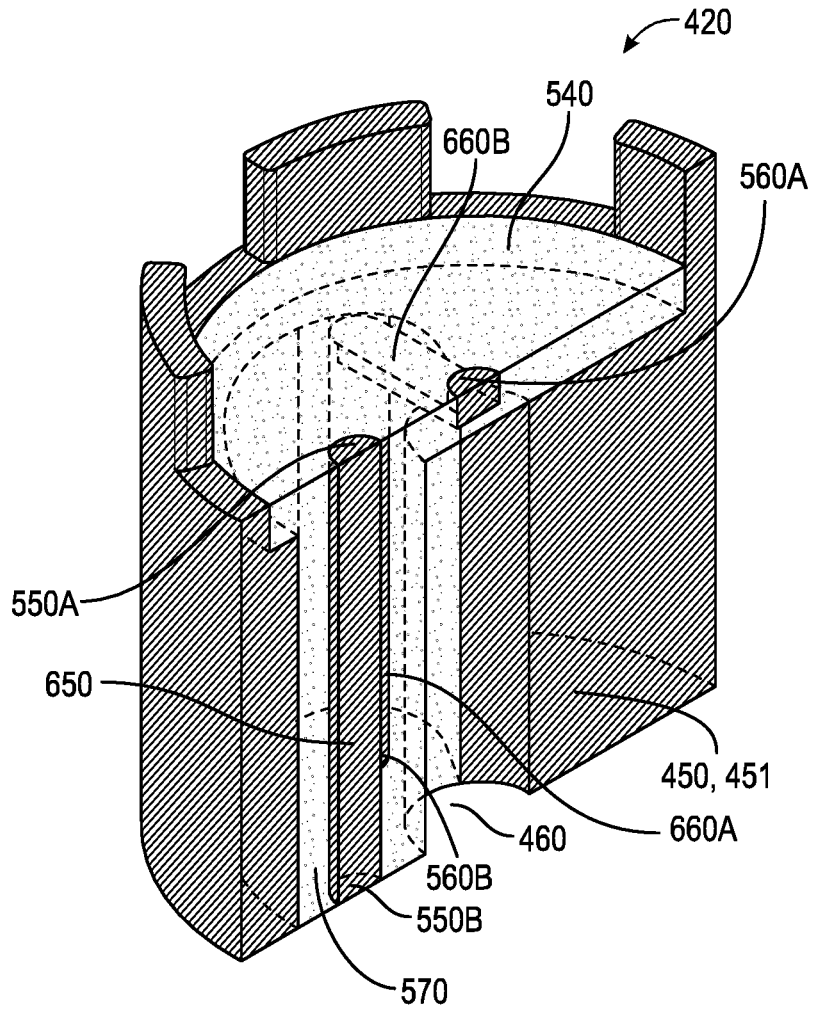
FIG. 6A is a diagrammatic, perspective, cross-sectional view of an example bottom portion of a sensor housing or sensor assembly, in accordance with at least one embodiment of the present disclosure.

FIG. 6A is a diagrammatic, perspective, cross-sectional view of an example bottom portion 420 of a sensor housing or sensor assembly 400, in accordance with at least one embodiment of the present disclosure. Visible are the acoustic backing layer 540, bottom electrode contacts 550A and 550B, top electrode contacts 560A and 560B, and core wire lumen 460. The bottom electrode contact 550A is connected to the bottom electrode contact 550B by an embedded conductor 650 within the insulating column 570. Similarly, the top electrode contact 560A is connected to the top electrode contact 560B by an embedded conductor 66A0 within the insulating column 570.

In an example, the crenelations 520, acoustic backing layer 540, bottom electrode contact 550A and top electrode contact 560A collectively form a bottom socket 590 (see FIG. 5A), configured to receive the sensor element 430 (see FIG. 4). In an example, the bottom socket 590 is configured such when the sensor element 430 is placed within the bottom socket 590, a bottom electrode 438 of the sensor element 430 (see FIG. 4) is in electrical contact with the bottom electrode contact 550A, and thus in electrical communication with the bottom electrode contact 550B via the embedded conductor 650. Contact between the bottom electrode 438 and the bottom electrode contact 550A may be direct, or may be through solder, conductive paste, conductive adhesive, conductive ink, or other conductive medium. Similarly, the bottom socket 590 may be configured such that the top contact electrode 560A is in electrical contact with an embedded conductor 760A of the top portion 410 (see FIG. 7), and thus in electrical communication with the top electrode 436 of the sensor element 430. The top electrode contact 560A is also shown as being in contact with the top electrode contact 560B via the embedded conductors 660A (positioned within the insulating column 570) and 660B (positioned within the acoustic backing layer 540).

The bottom portion 420 comprises an interior portion 450 which may, in some embodiments, comprise the conductive material, the dielectric material, or combinations thereof. In other embodiments, the interior portion 450 may be hollow, or may be partially or completely filled with an insulative adhesive or potting material 451 during assembly of the sensor housing or sensor assembly 400.

Figure 6B:
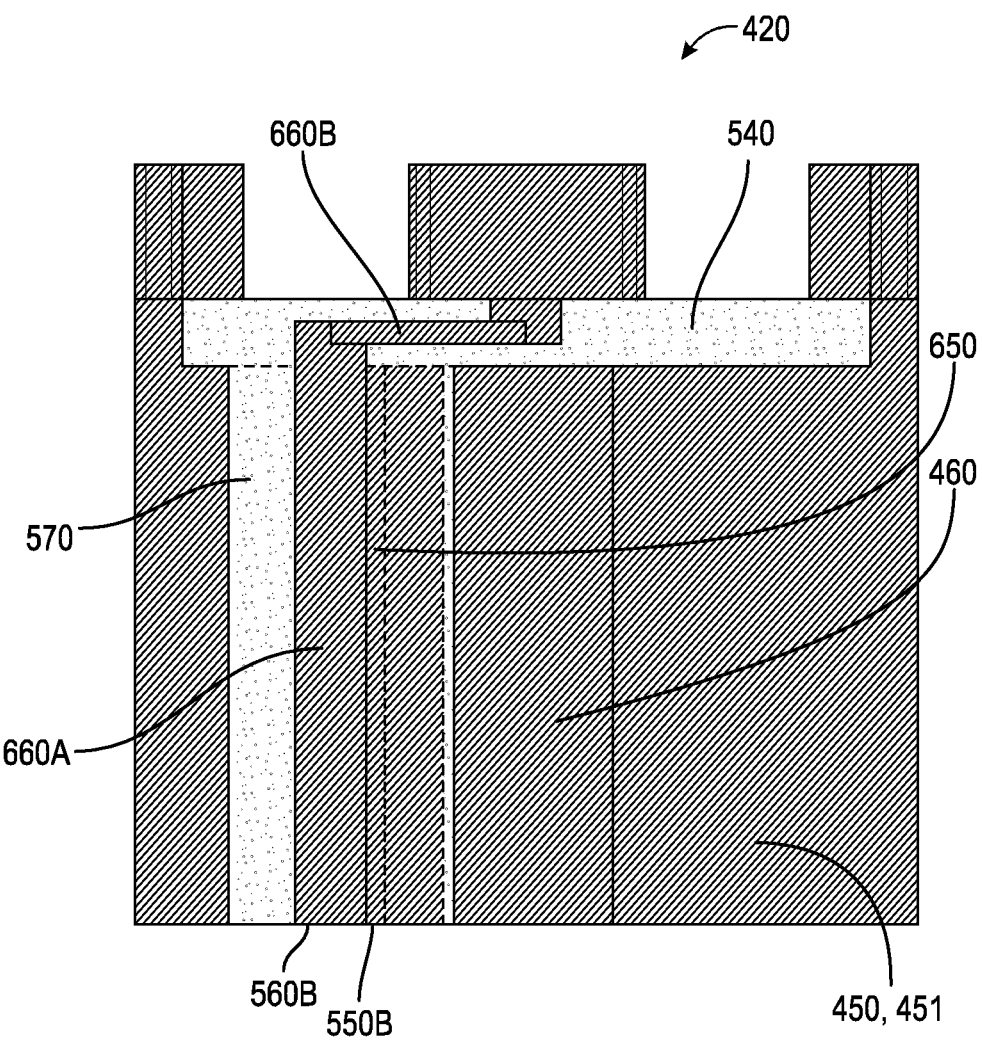
FIG. 6B is a diagrammatic, side cross-sectional view of an example bottom portion of a sensor housing or sensor assembly, in accordance with at least one embodiment of the present disclosure.

FIG. 6B is a diagrammatic, side cross-sectional view of an example bottom portion 420 of a sensor housing or sensor assembly 400, in accordance with at least one embodiment of the present disclosure. Visible are the acoustic backing layer 540, bottom electrode contacts 550A and 550B, top electrode contacts 560A and 560B, core wire lumen 460, bottom electrode contact 550A, bottom electrode contact 550B, embedded conductors 650, 660A, and 660B, insulating column 570, and interior portion 450. Embedded conductors 650 and 660a are embedded within insulating column 570.

Figure 7:
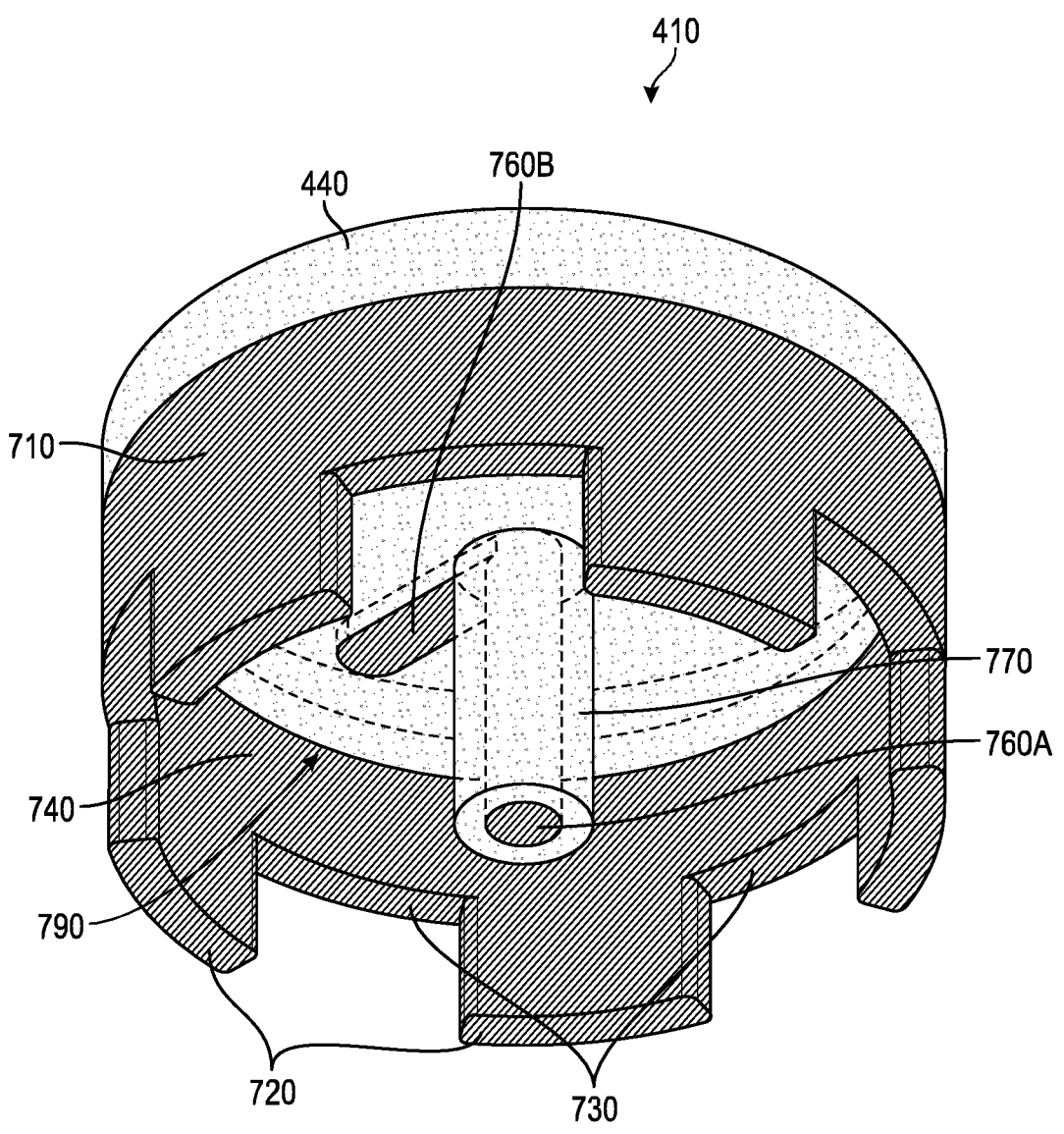
FIG. 7 is a diagrammatic, bottom perspective view of an example top portion 410 of a sensor housing or sensor assembly, in accordance with at least one embodiment of the present disclosure.

FIG. 7 is a diagrammatic, bottom perspective view of an example top portion 410 of a sensor housing or sensor assembly 400, in accordance with at least one embodiment of the present disclosure. In the example shown in FIG. 7, the top portion 410 includes an acoustic matching layer 440, sidewall 710, crenelations 720 and recesses 730, embedded conductor 760A, top electrode contact 760B, and insulating central post 770.

In an example, the top portion 410 is generally cylindrical in shape, to facilitate movement through blood vessels or other body lumens, although other shapes (e.g., polygonal prisms or other appropriate shapes) may be used instead or in addition. The top portion 410 includes a sidewall 710, which may in some cases be similar to side surface 274 of FIG. 2. In the example shown in FIG. 7, the sidewall 710 is terminated on a lower edge by crenelations 720, which are interspersed with recesses 730. Any number of crenelations 720 and recesses 730 may be used, from one to several dozen, although ranges between 3 and 8 may be preferred. In an example, the crenelations 720 and recesses 730 interlock with crenelations 520 and recesses 530 of the bottom portion 420 (see FIG. 5A), to arrest rotation of the top portion 410 and bottom portion 420 with respect to one another. It should be understood that these particular features are shown here for exemplary purposes. Other arresting or interlocking features may be used instead or in addition, including but not limited to pegs and indentations, saw teeth, threads, pins and grooves, etc.

In an example, the sidewall 710, crenelations 720, recesses 730, and contacts embedded conductor 760A, and top electrode contact 760B are made of a conductive material such as a metal, a doped semiconductor, a doped ceramic, or a doped polymer. In other examples, the sidewall 710, crenelations 720, and recesses 730 are made of an insulating material. In some embodiments, the outer surface of the sidewall 710 is a patient-contacting surface that may, for example, come into contact with the walls of a blood vessel. For this reason, it may be desirable for the sidewall 710 to present a smooth, atraumatic outer surface that moves easily through blood vessels without causing damage.

In an example, the crenelations 720, acoustic matching layer 440, embedded conductor 760A, top electrode contact 760B, and central post 770 collectively form a top socket 790, configured to receive the sensor element 430 (see FIG. 4). In an example, when the sensor element 430 is placed within the top socket 790, the central post 770 runs through the central lumen 435 of the sensor element 430 (see FIG. 4). The central post can be sized and shaped such that when fitted within the central lumen 435 of the sensor element 430, it arrests the sensor element 430 from lateral motion (e.g., motion perpendicular to the longitudinal axis of the guidewire). This can, for example, prevent the sensor element 430 from contacting the sidewall 710, which may help in electrically isolating the sensor element 430 from the sidewall 710, and also in providing an empty space 450 between the sensor element 430 and the sidewall 710, that can be filled with an adhesive or potting material 451 (see FIG. 4).

In the example shown in FIG. 7, the embedded conductor 760A runs through a central portion of the insulating central post 770, but is in electrical contact with top electrode contact 760B. In an example, the top socket 790 is configured such when the sensor element 430 is placed within the top socket 790, the top electrode 436 of the sensor element 430 (see FIG. 4) is in electrical contact with the top electrode contact 760B of the top portion 410, and thus in electrical communication with the embedded conductor 760A. In an example, when the top portion 410 and bottom portion 420 are fitted together, with the sensor element 430 fitted within the top socket 790 and bottom socket 590 (see FIG. 5A), the embedded conductor 760A is in electrical contact with the top electrode contact 560A of the bottom portion 420 (see FIG. 6A). Thus, the top electrode 436 of the sensor element 430 is in electrical communication with the top electrode contact 560B (see FIG. 5B), and thus in electrical communication with the PIM 304 (see FIG. 1) as described above. Contact between the embedded conductor 760A of the top portion 410 and top electrode contact 560A of the bottom portion may be direct, or may be through solder, conductive paste, conductive adhesive, conductive ink, or other conductive medium.

Thus, it can be seen that the sensor housing or sensor assembly 400 provides two separate conduction paths that are different from and electrically isolated from one another. A distal conduction path extends from the top electrode contact 560B of the bottom portion to the top electrode 436 of the sensor element 430 via embedded conductor 660A, top electrode contact 560A, and embedded conductors 760A and 760B. Similarly, a proximal conduction path extends from the bottom electrode contact 550B of the bottom portion to the bottom electrode 438 of the sensor element 430 via embedded conductor 650 and bottom electrode contact 550A (see FIGS. 4,6A, and 6B).

It is noted that the configuration shown in FIG. 7 is directed to a sensor element 430 that includes a top electrode and that does not include conductive traces on its surface that are capable of activating the top electrode. A person of ordinary skill in the art will appreciate that the sensor element 430 may have side electrodes rather than top and bottom electrodes, may have multiple electrodes, and/or may include surface traces in electrical communication with one or more electrodes. Some embodiments of the top portion 410 and/or bottom portion 420 may therefore not require the top electrode contact 760B, the central post 770, or the embedded conductor 760A, or may include other, related features intended to provide electrical communication between one or more electrodes of the sensor element 430 and the top electrode contact 560B of the bottom portion 420, and thus to the PIM 304 as described above.

Figures 8A, 8B:
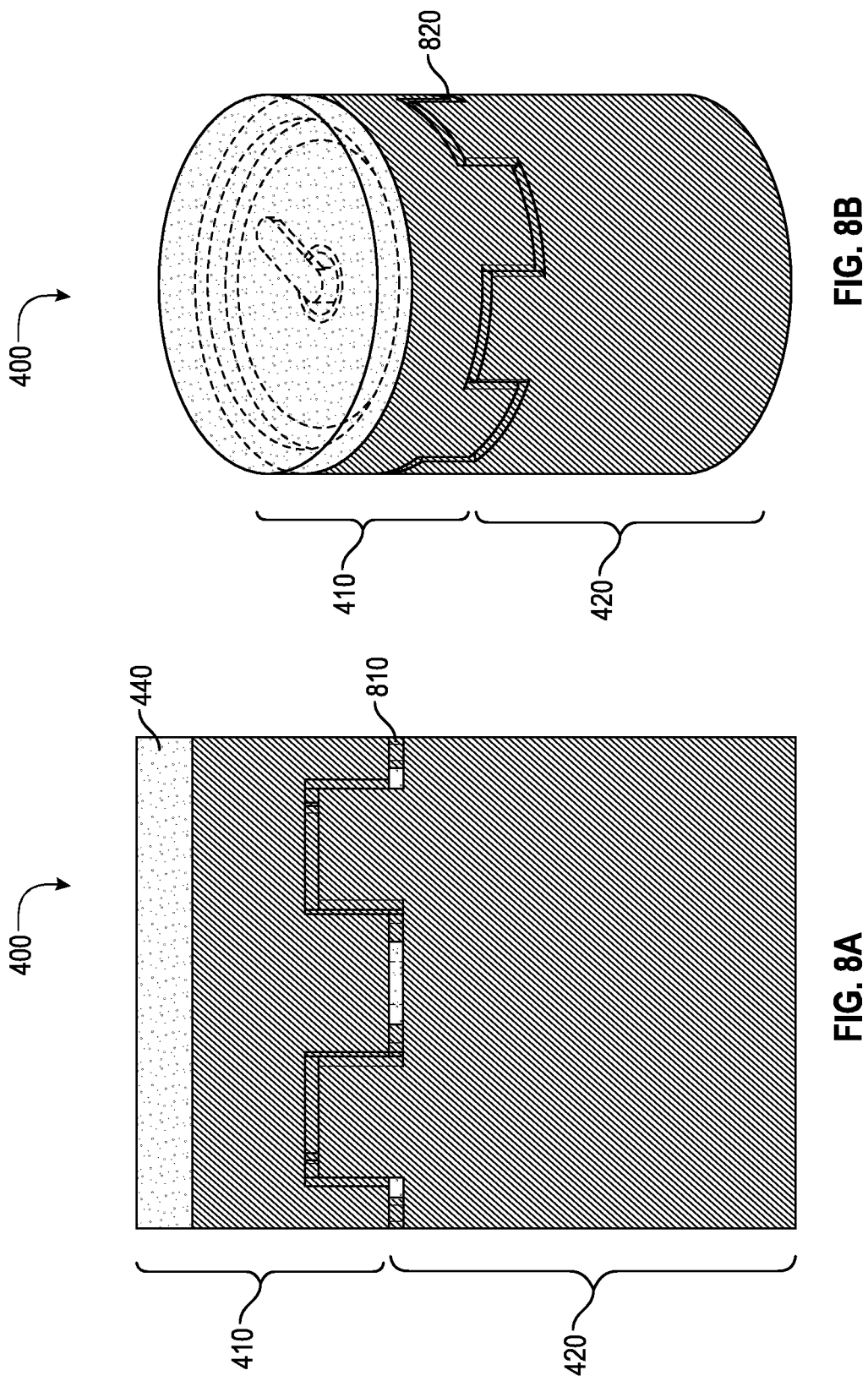
FIG. 8A is a diagrammatic side view of an example sensor housing or sensor assembly, in accordance with at least one embodiment of the present disclosure.
FIG. 8B is a diagrammatic side view of an example completed sensor housing or sensor assembly, in accordance with at least one embodiment of the present disclosure.

FIG. 8A is a diagrammatic side view of an example sensor housing or sensor assembly 400, in accordance with at least one embodiment of the present disclosure. In the example shown in FIG. 8A, the top portion 410 and bottom portion 420 have been fitted together around the sensor element 430 (see FIG. 4), as described above, such that their crenelations and recesses interlock. In some embodiments, a gap 810 may exist between the top portion 410 and bottom portion 420. This gap 810 may exist for example because the crenelations and recesses of the top portion 410 and bottom portion 420 are fabricated in slightly different sizes, such that manufacturing tolerances do not cause them to fit too tightly together. In other cases, the gap 810 may exist because the top portion 410 and bottom portion 420 have not yet been pressed all the way together. In some embodiments, the gap 810 may be anywhere from about 5 microns to about 20 microns, although other values both larger and smaller may be used instead or in addition.

In some embodiments, an insulative adhesive or potting material 451 (see FIG. 4) may be introduced (e.g., through injection, immersion, etc.) through the gap 810 to fill hollow spaces within at least the top portion 410 and bottom portion 420. The top portion 410 and bottom portion 420 may then be pressed together as fully as their geometry permits, and the potting material or adhesive may be allowed to cure or harden, resulting in a completed sensor housing or sensor assembly 400.

FIG. 8B is a diagrammatic side view of an example completed sensor housing or sensor assembly 400, in accordance with at least one embodiment of the present disclosure. In the example shown in FIG. 8B, the top portion 410 and bottom portion 420 have been fully pressed together. If an adhesive or potting material 451 (see FIG. 2) has been introduced to the interior of the sensor housing or sensor assembly 400 and allowed to cure or harden, the top portion 410 may be fixedly attached to the bottom portion 420 such that the tensor housing or sensor assembly 400 is fully assembled. The sensor housing or sensor assembly 400 may then be connected to filars of the multi-filar electrical conductor bundle 230 and the distal core wire 210 (see FIG. 2), as described above.

In some embodiments, all conductive elements of the sensor housing or sensor assembly 400 may be fabricated (e.g., 3D printed layer-by-layer) from a single conductive material, such as a metal, doped semiconductor, doped ceramic, or doped polymer. Such conductive elements may for example include sidewalls 510 and 710, crenelations 520 and 720, recesses 530 and 730, electrical contacts 550A, 550B, 560A, 560B, and 760B, embedded conductors 650, 660A, and 760A, and core wire lumen 460. In other embodiments, different conductive elements may be fabricated from different conductive materials with properties (e.g., electrical, mechanical, or acoustic properties) that are advantageous for each element.

In some embodiments, all insulating or dielectric elements of the sensor housing or sensor assembly 400 may be fabricated (e.g., 3D printed layer-by-layer) from a single insulating material, such as a polymer, ceramic, or composite. Fabrication of the insulating or dielectric elements may occur simultaneously with fabrication of the conductive elements, for example by a 3D microprinter capable of depositing at least two different materials (e.g., one conductive and one insulative). Such insulating elements may for example include the acoustic matching layer 440, central post 770, acoustic backing layer 540, and insulating column 570. In other embodiments, different insulating elements may be fabricated from different insulative materials with properties (e.g., electrical, mechanical, or acoustic properties) that are advantageous for each element.

For example, an acoustic matching layer may facilitate propagation of ultrasound waves/echoes because it has an impedance value similar to the patient anatomy. Ultrasound energy propagates better when there is such a gradual transition in impedance. It may therefore be desirable for the acoustic matching layer 440 to be made from a material that is highly transparent to ultrasonic waves, and that has an acoustic impedance within a particular range (e.g., midway between the acoustic impedance of the sensing element and the tissue being imaged), or even multiple acoustic matching layers 440 made from materials with different acoustic impedances. Furthermore, since the acoustic matching layer 440 may be a patient-contacting surface, it may in some cases be selected from biocompatible materials with desirable hydrophilic or hydrophobic properties. Conversely, an acoustic backing layer may attenuate ultrasound energy in undesired directions (e.g., backward or inward), so that ultrasound energy propagates in primarily in the desired direction (e.g., forward or outward). It may thus be desirable for the acoustic backing layer 540 to be made from a material different from the acoustic matching layer, that is either highly absorptive or highly reflective to ultrasound waves. Materials may also be selected for mutual adhesion, to minimize the chance of parts or layers delaminating from one another. Thus, in some embodiments, the top portion 410 may be fabricated from a particular advantageous combination of conductor and insulator, while the bottom portion 420 may be fabricated from a different advantageous combination that includes a different conductor and/or a different insulator.

Multi-component 3D microprinting can allow the construction of precise, complex microstructures that include both conductive and insulating elements, with feature sizes or voxel sizes of 10 microns or less. Thus, assemblies such as the top portion 410 and bottom portion 420 can each be fabricated as a single piece, rather than assembled from multiple pieces. This allows the sensor housing or sensor assembly 400 to comprise just two main pieces, plus assembly materials such as solder, adhesives, or potting compounds. The resulting assembly process may be significantly cheaper, faster, easier, more reliable, and more repeatable than was possible with previous systems, while the sensor assembly 400 itself may be more physically robust than the sensor assemblies of previous intravascular sensing systems.

Figure 9:
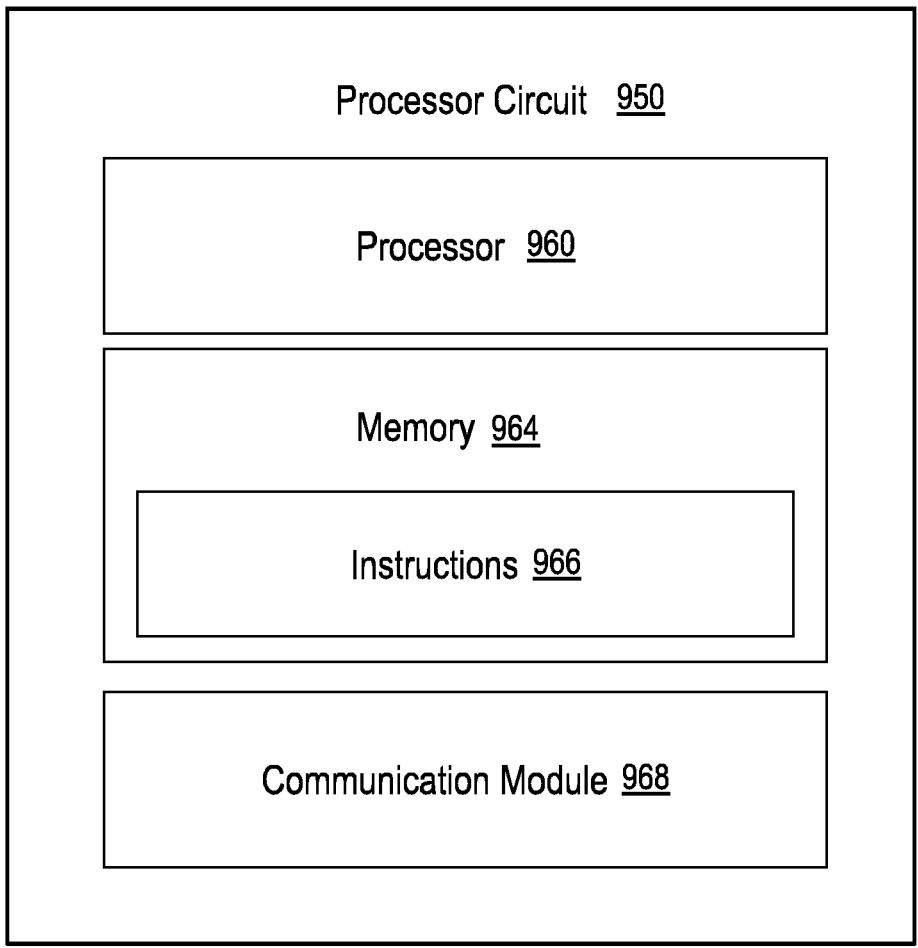
FIG. 9 is a schematic diagram of a processor circuit, in accordance with at least one embodiment of the present disclosure.

FIG. 9 is a schematic diagram of a processor circuit 950, according to at least one embodiment of the present disclosure. The processor circuit 950 may be implemented in the intravascular sensing system 100, processing system 306, or other devices or workstations (e.g., third-party workstations, network routers, etc.), or on a cloud processor or other remote processing unit, as necessary to implement the devices, systems, and methods disclosed herein. As shown, the processor circuit 950 may include a processor 960, a memory 964, and a communication module 968. These elements may be in direct or indirect communication with each other, for example via one or more buses.

The processor 960 may include a central processing unit (CPU), a digital signal processor (DSP), an ASIC, a controller, or any combination of general-purpose computing devices, reduced instruction set computing (RISC) devices, application-specific integrated circuits (ASICs), field programmable gate arrays (FPGAs), or other related logic devices, including mechanical and quantum computers. The processor 960 may also comprise another hardware device, a firmware device, or any combination thereof configured to perform the operations described herein. The processor 960 may also be implemented as a combination of computing devices, e.g., a combination of a DSP and a microprocessor, a plurality of microprocessors, one or more microprocessors in conjunction with a DSP core, or any other such configuration.

The memory 964 may include a cache memory (e.g., a cache memory of the processor 960), random access memory (RAM), magnetoresistive RAM (MRAM), read-only memory (ROM), programmable read-only memory (PROM), erasable programmable read only memory (EPROM), electrically erasable programmable read only memory (EEPROM), flash memory, solid state memory device, hard disk drives, other forms of volatile and non-volatile memory, or a combination of different types of memory. In an embodiment, the memory 964 includes a non-transitory computer-readable medium. The memory 964 may store instructions 966. The instructions 966 may include instructions that, when executed by the processor 960, cause the processor 960 to perform the operations described herein. Instructions 966 may also be referred to as code. The terms "instructions" and "code" should be interpreted broadly to include any type of computer-readable statement(s). For example, the terms "instructions" and "code" may refer to one or more programs, routines, subroutines, functions, procedures, etc. "Instructions" and "code" may include a single computer-readable statement or many computer-readable statements.

The communication module 968 can include any electronic circuitry and/or logic circuitry to facilitate direct or indirect communication of data between the processor circuit 950, and other processors or devices. In that regard, the communication module 968 can be an input/output (I/O) device. In some instances, the communication module 968 facilitates direct or indirect communication between various elements of the processor circuit 950 and/or the intravascular measurement system 100. The communication module 968 may communicate within the processor circuit 950 through numerous methods or protocols. Serial communication protocols may include but are not limited to US SPI, I²C, RS-232, RS-485, CAN, Ethernet, ARINC 429, MODBUS, MIL-STD-1553, or any other suitable method or protocol. Parallel protocols include but are not limited to ISA, ATA, SCSI, PCI, IEEE-488, IEEE-1284, and other suitable protocols. Where appropriate, serial and parallel communications may be bridged by a UART, USART, or other appropriate subsystem.

External communication (including but not limited to software updates, firmware updates, preset sharing between the processor and central server, or readings from the ultrasound device) may be accomplished using any suitable wireless or wired communication technology, such as a cable interface such as a USB, micro USB, Lightning, or FireWire interface, Bluetooth, Wi-Fi, ZigBee, Li-Fi, or cellular data connections such as 2G/GSM, 3G/UMTS, 4G/LTE/WiMax, or 5G. For example, a Bluetooth Low Energy (BLE) radio can be used to establish connectivity with a cloud service, for transmission of data, and for receipt of software patches. The controller may be configured to communicate with a remote server, or a local device such as a laptop, tablet, or handheld device, or may include a display capable of showing status variables and other information. Information may also be transferred on physical media such as a USB flash drive or memory stick.

Accordingly, it can be seen that the present disclosure improves the operation and assembly process of flow-sensing guidewire devices and systems, by providing a two-piece sensor housing with built-in wiring, electrical contacts, and acoustic matching and backing layers.

The present disclosure may for example implemented for a flow-sensing guidewire, such as the Philips FloWire (Doppler guide wire) or the Philips ComboWire™ that provides simultaneous pressure and flow information. It can also be applied to new flow modalities under the development, both for existing devices and for devices hereinafter developed, either with single transducers or multiple transducers, and comprising either a flow-only sensor or a flow sensor combined with a pressure sensor, or with other sensing modalities.

A number of variations are possible on the examples and embodiments described above. For example, one or more surfaces of the multi-component sensor housing may include coatings such as hydrophobic, hydrophillic, lubricious, anti-scratch, or other coatings. Some components shown as conductive may also function if made from insulators, and vice-versa. Some components shown as insulative, such as the central post or insulating column, may be deleted, and their insulative properties introduced via insulating adhesives or potting compounds. Adhesives or potting compounds may be selected based on their mechanical, electrical, or acoustic properties. The acoustic matching layer may be replaced with an optically transparent or translucent material, or a material transparent to other types of radiation, the acoustic backing layer may be replaced with an optically reflective or optically absoptive material, or a material reflective or absorptive to other types of radiation, and the sensor element 430 may be replaced with an optical emitter, optical sensor, or other type of sensor.

The logical operations making up the embodiments of the technology described herein are referred to variously as operations, steps, objects, elements, components, or modules. It should be understood that these may be arranged or performed in any order, unless explicitly claimed otherwise or a specific order or arrangement is inherently necessitated by the claim language. It should further be understood that the described technology may be employed in single-use and multi-use electrical and electronic devices for medical or nonmedical use.

All directional references e.g., upper, lower, inner, outer, upward, downward, left, right, lateral, front, back, top, bottom, above, below, vertical, horizontal, clockwise, counterclockwise, proximal, and distal are only used for identification purposes to aid the reader's understanding of the claimed subject matter, and do not create limitations, particularly as to the position, orientation, or use of the multi-component sensor housing. Connection references, e.g., attached, coupled, connected, and joined are to be construed broadly and may include intermediate members between a collection of elements and relative movement between elements unless otherwise indicated. As such, connection references do not necessarily imply that two elements are directly connected and in fixed relation to each other. The term "or" shall be interpreted to mean "and/or" rather than "exclusive or." The word "comprising" does not exclude other elements or steps, and the indefinite article "a" or "an" does not exclude a plurality. Unless otherwise noted in the claims, stated values shall be interpreted as illustrative only and shall not be taken to be limiting.

The above specification, examples and data provide a complete description of the structure and use of exemplary embodiments of the multi-component sensor housing as defined in the claims. Although various embodiments of the claimed subject matter have been described above with a certain degree of particularity, or with reference to one or more individual embodiments, those skilled in the art could make numerous alterations to the disclosed embodiments without departing from the spirit or scope of the claimed subject matter.

Still other embodiments are contemplated. It is intended that all matter contained in the above description and shown in the accompanying drawings shall be interpreted as illustrative only of particular embodiments and not limiting. Changes in detail or structure may be made without departing from the basic elements of the subject matter as defined in the following claims.

What is claimed is:

1. An intraluminal device, comprising:
   a flexible elongate member configured to extend in a longitudinal direction within a body lumen of a patient;
   a sensor disposed at a distal region of the flexible elongate member, wherein the sensor is configured obtain intraluminal data associated with the body lumen; and
   a housing at least partially surrounding the sensor, wherein the housing comprises a distal portion fixedly attached to a proximal portion,
   wherein the distal portion and the proximal portion are distinct from one another,
   wherein the distal portion comprises a first conductive material and a first dielectric material,
   wherein the proximal portion comprises a second conductive material and a second dielectric material, and
   wherein the first conductive material and the second conductive material are in electrical communication with the sensor.

2. The intraluminal device of claim 1, wherein the sensor comprises an ultrasound transducer configured to emit ultrasound waves while positioned within the body lumen and to receive echoes associated with the emitted ultrasound waves.

3. The intraluminal device of claim 1, wherein the distal portion of the housing further comprises an acoustic matching layer formed of the first dielectric material.

4. The intraluminal device of claim 1, wherein the proximal portion of the housing further comprises an acoustic backing layer formed of the second dielectric material.

5. The intraluminal device of claim 1, wherein:
   the sensor comprises a first electrode and a second electrode;
   the proximal portion of the housing comprises a first electrical contact and a second electrical contact formed of the second conductive material; and
   the proximal portion of the housing or distal portion of the housing comprise:
   a first embedded conduction path formed of the first conductive material or the second conductive material and in electrical communication with the first electrical contact and the first electrode; and
   a second embedded conduction path formed of the first conductive material or the second conductive material and in electrical communication with the second electrical contact and the second electrode.

6. The intraluminal device of claim 5, wherein the first embedded conduction path and second embedded conduction path are at least partially surrounded by the first dielectric material or the second dielectric material.

7. The intraluminal device of claim 5, wherein:

the first electrical contact is attached to and in electrical communication with a first conductive filar positioned along the flexible elongate member; and the second electrical contact is attached to and in electrical communication with a second conductive filar positioned along the flexible elongate member.

8. The intraluminal device of claim 1, wherein the distal portion of the housing includes an arresting feature that interacts with an arresting feature of the proximal portion of the housing to arrest rotation of the distal portion with respect to the proximal portion.

9. The intraluminal device of claim 1, wherein the sensor comprises a central lumen aligned with the longitudinal direction, and wherein the distal portion of the housing or the proximal portion of the housing comprises a central post passing through at least a portion of the central lumen, such that the sensor is arrested from lateral motion with respect to the distal portion and the proximal portion.

10. The intraluminal device of claim 1, wherein the flexible elongate member comprises a core wire, and wherein the proximal portion includes a core wire lumen configured to receive a distal portion of the core wire.

11. The intraluminal device of claim 10, wherein the distal portion of the core wire is fixedly attached within the core wire lumen.

12. The intraluminal device of claim 1, wherein the proximal portion of the housing is fixedly attached to the distal portion of the housing by an adhesive.

13. The intraluminal device of claim 12, wherein at least some interior volume of the proximal portion of the housing or the distal portion of the housing is filled by the adhesive.

14. The intraluminal device of claim 13, wherein an outer surface of the sensor is fixedly attached to an inner surface of the proximal portion of the housing or the distal portion of the housing by the adhesive.

15. The intraluminal device of claim 13, wherein a proximal edge of the distal portion of the housing forms a gap with a distal edge of the proximal portion of the housing.

16. The intraluminal device of claim 15, wherein the gap is at least partially filled by the adhesive.

17. The intraluminal device of claim 1, wherein the first conductive material and the second conductive material are a same material.

18. The intraluminal device of claim 1, wherein the first dielectric material is configured to provide acoustic impedance, and wherein the second dielectric material is configured to provide acoustic absorptivity or reflectivity.

19. The intraluminal device of claim 1, wherein the sensor disposed at the distal region of the flexible elongate member facing in the longitudinal direction, and wherein the sensor is configured to emit ultrasound waves in the longitudinal direction.

20. An apparatus, comprising:

an intravascular guidewire comprising:

a flexible elongate member configured to extend in a longitudinal direction within a blood vessel of a patient; and a flow sensor disposed at a distal region of the flexible elongate member, wherein the flow sensor comprises:

an ultrasound transducer configured to emit ultrasound waves in the longitudinal direction while positioned within a body lumen and to receive echoes associated with the ultrasound waves;

a first electrode;

a second electrode; and a housing at least partially surrounding the flow sensor, wherein the housing comprises a distal portion fixedly attached to a proximal portion, wherein the distal portion and the proximal portion are distinct from one another wherein the distal portion of the housing comprises:

a first dielectric material;

an acoustic matching layer comprising the first dielectric material;

a distal conduction path comprising a first conductive material and in electrical communication with the first electrode of the flow sensor, and wherein the proximal portion of housing comprises:

a second dielectric material;

an acoustic backing layer comprising the second dielectric material;

a proximal conduction path comprising a second conductive material and in electrical communication with the second electrode of the sensor element;

a first electrical contact positioned on a proximal surface of the proximal portion and in electrical communication with the proximal conduction path; and a second electrical contact positioned on the proximal surface of the proximal portion and in electrical communication with the distal conduction path.

\* \* \* \* \*